(12) United States Patent
Du

(10) Patent No.: US 6,622,726 B1
(45) Date of Patent: Sep. 23, 2003

(54) BREATHING APPARATUS AND METHOD

(75) Inventor: Hong-Lin Du, Santa Ana, CA (US)

(73) Assignee: Newport Medical Instruments, Inc., Costa Mesa, CA (US)

(*) Notice: Subject to any disclaimer, the term of this patent is extended or adjusted under 35 U.S.C. 154(b) by 68 days.

(21) Appl. No.: 09/690,970

(22) Filed: Oct. 17, 2000

(51) Int. Cl.[7] .......................... A61M 16/00; A62B 7/04; F16K 31/26
(52) U.S. Cl. ...................... 128/204.26; 128/204.21; 128/204.23; 128/205.11
(58) Field of Search .................. 128/204.21, 204.23, 128/204.26, 205.11, 205.14, 205.24, 207.12, 207.14, 207.18

(56) References Cited

U.S. PATENT DOCUMENTS

| | | | | |
|---|---|---|---|---|
| 4,020,834 A | * | 5/1977 | Bird | 128/204.25 |
| 4,141,356 A | * | 2/1979 | Smargiassi | 128/204.23 |
| 4,357,936 A | * | 11/1982 | Ellestad et al. | 128/204.23 |
| 4,681,099 A | | 7/1987 | Sato et al. | |
| 4,706,664 A | * | 11/1987 | Snook et al. | 128/204.23 |
| 5,148,802 A | * | 9/1992 | Sanders et al. | 128/204.18 |
| 5,199,424 A | * | 4/1993 | Sullivan et al. | 128/204.18 |
| 5,271,389 A | * | 12/1993 | Isaza et al. | 128/204.21 |
| 5,458,137 A | * | 10/1995 | Axe et al. | 128/204.21 |
| 5,535,738 A | * | 7/1996 | Estes et al. | 128/204.23 |
| 5,542,416 A | * | 8/1996 | Chalvignac | 128/204.23 |
| 5,598,838 A | * | 2/1997 | Servidio et al. | 128/204.21 |
| 5,617,846 A | * | 4/1997 | Graetz et al. | 128/204.21 |
| 5,660,171 A | * | 8/1997 | Kimm et al. | 128/204.21 |
| 5,794,615 A | * | 8/1998 | Estes | 128/204.23 |
| 5,803,065 A | * | 9/1998 | Zdrojkowski et al. | 128/204.23 |
| 5,813,399 A | * | 9/1998 | Isaza et al. | 128/204.21 |
| 5,823,187 A | | 10/1998 | Estes et al. | |
| 5,845,636 A | * | 12/1998 | Gruenke et al. | 128/204.23 |
| 5,862,802 A | * | 1/1999 | Bird | 128/204.18 |
| 6,095,140 A | * | 8/2000 | Poon et al. | 128/204.18 |
| 6,397,845 B1 | * | 6/2002 | Burton | 128/204.23 |
| 6,398,739 B1 | * | 6/2002 | Sullivan et al. | 600/529 |

FOREIGN PATENT DOCUMENTS

| | | |
|---|---|---|
| WO | WO 95/32016 | 11/1995 |
| WO | WO 97/15343 | 5/1997 |

* cited by examiner

Primary Examiner—Weilun Lo
Assistant Examiner—Michael Mendoza
(74) Attorney, Agent, or Firm—Brown, Martin, Haller & McClain LLP

(57) ABSTRACT

A positive airway pressure assist breathing apparatus or ventilator system has a gas delivery unit, an inspiration line connected to the output of the gas delivery unit for connecting the gas delivery unit to a, patient during an inspiratory phase of each breath, and an expiratory unit for controlling exhausting of gases from the patient during an expiratory phase of each breath. A pressure sensor senses gas pressure in the system, and a control unit controls pressure of gas supplied to a patient in each inspiratory phase based on a pre-set target pressure. The control unit is arranged to calculate a boost pressure level periodically according to a determined patient breathlessness level, and to boost the pressure of gas supplied to the patient at the start of each inspiratory phase to the calculated boost pressure level higher than the pre-set target pressure, and to reduce the pressure back to the pre-set target pressure at a predetermined time after the start of the inspiratory phase and prior to the end of the inspiratory phase. Boost pressure is adjusted periodically based on each new determination of the patient breathlessness level.

19 Claims, 2 Drawing Sheets

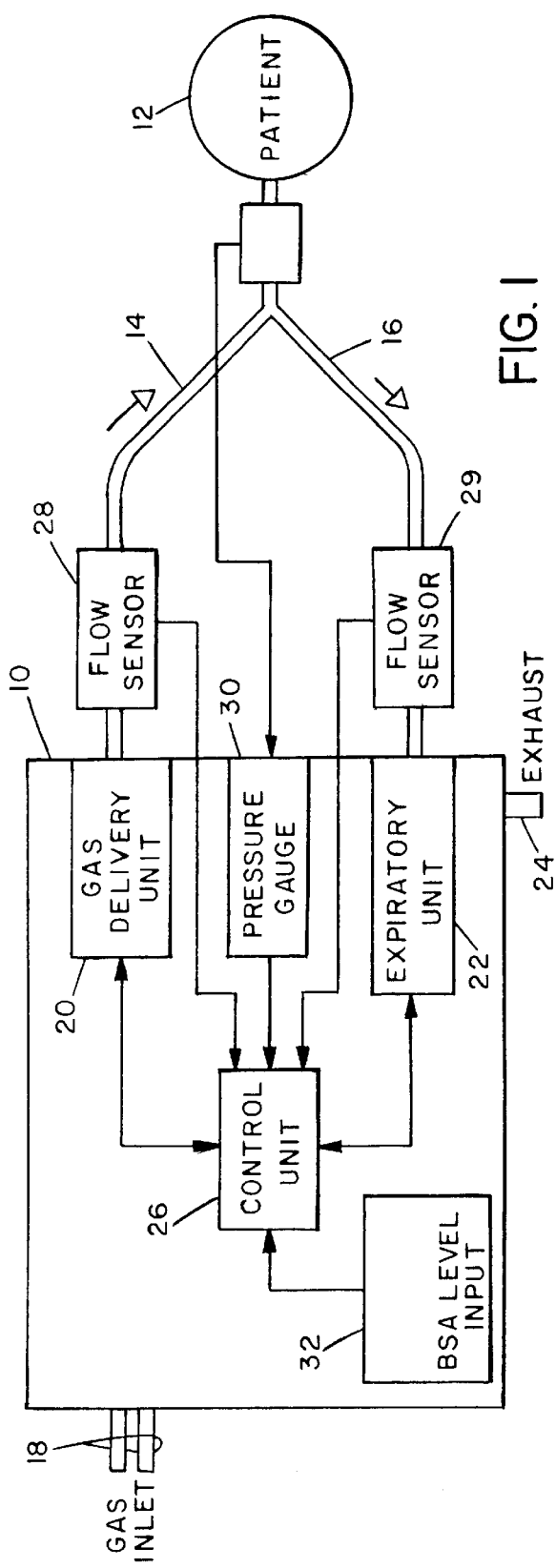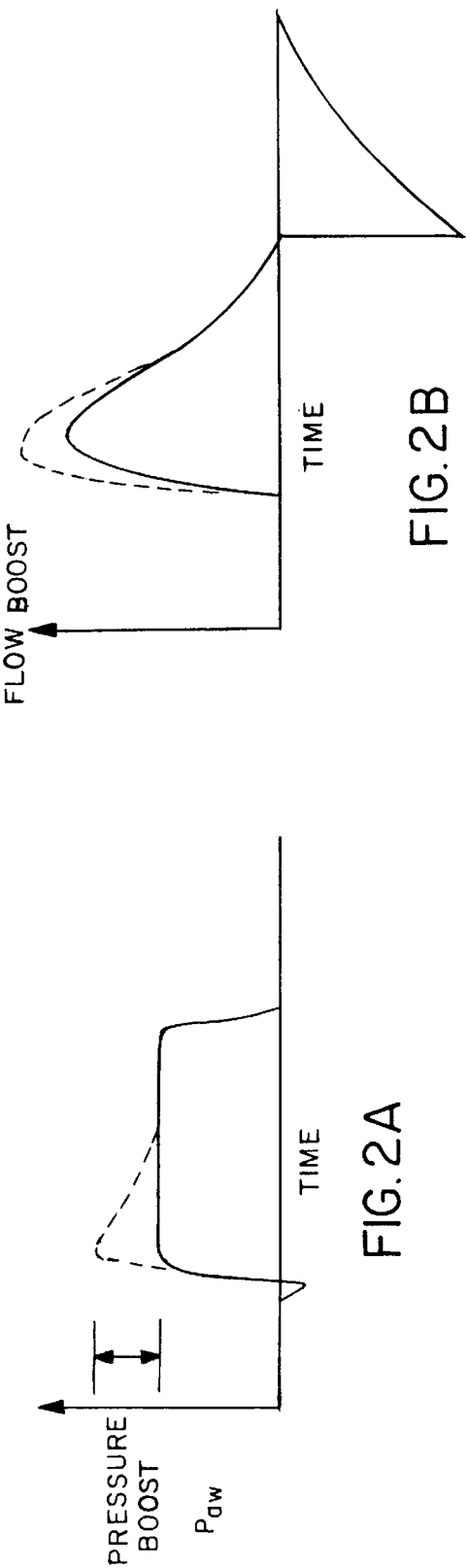

BREATHING APPARATUS AND METHOD

BACKGROUND OF THE INVENTION

The present invention relates generally to a breathing apparatus or ventilator and method for supplying inspiratory gases to a living being such as a human or animal patient, and is particularly concerned with relieving the breathless sensation often encountered by individuals on ventilators.

A breathing apparatus or ventilator is generally connected to a patient through a patient circuit having an inspiratory limb and an expiratory limb. The ventilator delivers gases to the patient from a gas delivery unit through the inspiratory limb during inspiration, and allows removal of expired gases through the expiratory limb during expiration. Pressure targeted ventilation is a type of ventilation in which the ventilator tries to reach a pre-set pressure level and maintain that level during the inspiration phase. There are two types of pressure targeted ventilation, called pressure control ventilation and pressure support ventilation, or PSV.

One problem with all types of ventilation is that patients sometimes feel breathless even though the work of breathing has been reduced significantly. This is because the amount of gas supplied by the ventilator at a certain time may not necessarily correspond to the patient's own effort to inhale, or the patient inspiratory muscle pressure change (Pmus). From the physiological standpoint, when the patient generates a certain level of Pmus, he would expect a certain level of flow into his airway. For the patient under mechanical ventilation, if the flow provided by the ventilator is much lower than that level at a given Pmus, the patient will feel breathless (or encounter a resistive load detection). This principle is described in a paper entitled "Effect of timing, flow, lung volume, and threshold pressures on resistive load detection" by Killian et al., Journal of Applied Physiology 1980; 49:958–963. It has also been found that the breathless sensation occurs more at the early phase of the inspiration than the late phase. In patients who have respiratory failure due to high airway resistance, additional resistance from the endotracheal tube and patient circuit, and/or reduced respiratory compliance, the flow as a function of patient Pmus falls below the threshold. In order to compensate for this, patients will increase their inspiratory effort, or Pmus, causing them to feel even more breathless.

The breathless sensation is a problem even in pressure targeted ventilation, since the patient effort is not taken into account in the control system of such ventilatory modes. The control system simply aims to maintain the set pressure level, or Paw, during the inspiratory phase, resulting in a quasi square pressure waveform.

Some other types of ventilation aim to take patient effort into account to some degree. Younes introduced proportional assist ventilation in his article "Proportional assist ventilation, a new approach to ventilatory support", American Review of Respiratory Diseases 1992;145(1):114–120, U.S. Pat. No. 5,044,362. During proportional assist ventilation, the ventilator is controlled in such a way that the pressure delivered at the airway increases in proportion to the patient spontaneous effort throughout the whole inspiration. The delivered pressure is controlled by two factors, flow assist (resistive gain) and volume assist (elastance gain).

Under proportional assist ventilation, the patient has a very high level of freedom and capability of controlling the ventilator, which can cause problems. For many patients in intensive care units, too much freedom may mean underventilation if the patient's inspiratory effort becomes weak, or overventilation if the patient's inspiratory effort becomes aggressive. Also, in proportional assist ventilation the ventilator control system may "run away" if volume assist is set below patient elastance. The ventilatory support during proportional assist ventilation is proportional to the patient muscle pressure throughout the whole inspiration. Therefore, in proportional assist ventilation, airway resistance and respiratory compliance values representative for the whole inspiratory phase must be accurately calculated for the purposes of accurate ventilator control and ventilatory management.

In the Drager Evita 4 ventilator, as described in the "Drager Evita 4 Operating Manual (Drager Medizintechnik GmbH, Lubeck Germany) there is a breath mode called "automatic tube compensation". When this mode is used, the user needs to set the endotracheal tube size (resistance factor) and the percentage of tube compensation. The ventilator will then try to overcome the resistance imposed by the endotracheal tube by adding more pressure than the set value, with the use of the anticipated endotracheal tube resistance. This does not take into account any information of patient effort in the adjustment of the compensation levels. The compensation level is fixed and is solely determined by the user-set endotracheal tube size and percentage of tube compensation.

SUMMARY OF THE INVENTION

It is an object of the present invention to provide a new and improved pressure targeted breathing apparatus and method which relieves the breathless sensation sometimes encountered by patients on ventilators.

According to one aspect of the present invention, a breathing apparatus for providing positive pressure assistance is provided, which comprises a source of breathing gas, an inspiration line for connecting the source to a patient during an inspiratory phase, an expiratory line for exhausting gases from the patient during an expiratory phase, a pressure sensor for sensing pressure in the system, and a control unit for controlling supply of gas to a patient in each inspiratory phase according to a pre-set target pressure, the control unit being programmed to determine the level of patient breathlessness at periodic intervals and to calculate a boost pressure above the pre-set target pressure based on the determined breathlessness level, and to boost the pressure (and accordingly the flow) of gas supplied to the patient at the start of each inspiratory phase to the most recently calculated boost pressure in order to reduce patient breathlessness, and reduce the pressure back to the target pressure at a predetermined time after the start of the inspiratory phase and prior to the end of the inspiratory phase.

The boost pressure level may be determined by a user-adjustable controller on the apparatus to a selected breathless sensation assist level, or BSA, and may also be varied in proportion to the detected occlusion pressure at the pressure sensor, or Paw, at a predetermined time after the start of inspiration with the patient airway being temporarily occluded, for example at 0.1 seconds after the onset of inspiration (Paw-0.1). Thus, for any selected BSA greater than zero, the pressure boost level will be varied in proportion to the BSA level and detected Paw-0.1 for a preceding measurement or preceding measurements, and will increase with increase in Paw-0.1. This is because research on the relationship between the airway occlusion pressure or Paw and the patient inspiratory effort, or Pmus, have indicated that there is a good consistency between the two pressures at the beginning of inspiration. (Conti, G. et al., American Journal of Respiration and Critical Care Medicine, 1996, 154:907–912). Thus, boosting of pressure (i.e., flow delivery) in proportion to Paw-0.1 can relieve the breathless sensation of ventilated patients.

In one exemplary embodiment of the invention, the pressure boost magnitude is gradually tapered down from the boost level back to the target pressure level at around the middle of the inspiration phase of the respiratory cycle. The control unit is set up to measure the Paw-0.1 value at periodic intervals, and can be measured by delaying the onset of the inspiratory gas delivery for a predetermined time after the ventilator is triggered, such as 0.1 seconds. This allows for a reliable Paw-0.1 measurement without causing significant patient awareness or discomfort. The measurement may be made at predetermined intervals, for example every 20 breaths or every 2 minutes, with appropriate readjustment of the pressure boost level after every measurement.

Instead of boosting the pressure of gas supplied, gas flow to the patient may instead be boosted directly by a corresponding amount.

According to another aspect of the present invention, a method of controlling the inspiratory phase in a pressure targeted ventilation system is provided, which comprises the steps of setting a target pressure level for the inspiratory phase, determining a boost pressure level higher than the pre-set target pressure level, periodically determining the level of patient breathlessness and adjusting the boost pressure in response to changes in the level of patient breathlessness, boosting the pressure supplied to the patient to the most recently calculated boost pressure level at the start of the inspiratory phase in order to relieve any breathless sensation encountered by a patient, and gradually reducing the pressure from the boost level back to the pre-set target level at a predetermined point in the inspiratory phase.

The step of determining a boost pressure level may be carried out at predetermined time intervals or for each nth breath, for example at 2 minute intervals or every 20 breaths, although other time or breath intervals may be selected. The boost pressure level may be determined based on two factors, one of which is a user selected breathless sensation assist (BSA) level, and the other of which is based on a detected patient airway occlusion pressure or Paw-t at a short time interval of t seconds after the onset of a patient inspiratory effort. In one example, Paw-t was measured by delaying the onset of inspiratory gas delivery for a predetermined time, such as 0.1 seconds, after the ventilator was triggered, and analyzing the pressure detected by the pressure sensor for this time period, using the most linear segment of the slope of pressure vs. time to determine Paw-t, or Paw-0.1 where the time interval is selected to be 0.1 seconds.

This invention uses the patient's physiological information, as determined by the periodic measurement of Paw-0.1, as well as a user adjustable BSA level, in order to boost the pressure of gas supplied to the patient to a predetermined level at the start of each breath or inspiration. This will overcome or reduce any breathless sensation which may otherwise be encountered by the patient if their inspiratory muscle pressure change does not result in an expected airway flow, as may be the case when a set and unchanging pressure level is used throughout the inspiratory phase.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which:

FIG. 1 is a schematic block diagram of a pressure targeted ventilation system according to an exemplary embodiment of the invention;

FIG. 2a illustrates the variation of pressure with time in an inspiration phase of the ventilator breathing cycle, illustrating an exemplary pressure boost at the start of inspiration using the system of FIG. 1;

FIG. 2b illustrates the resultant flow boost to a patient using the pressure boost of FIG. 2a;

DETAILED DESCRIPTION OF THE DRAWINGS

Figure 3:
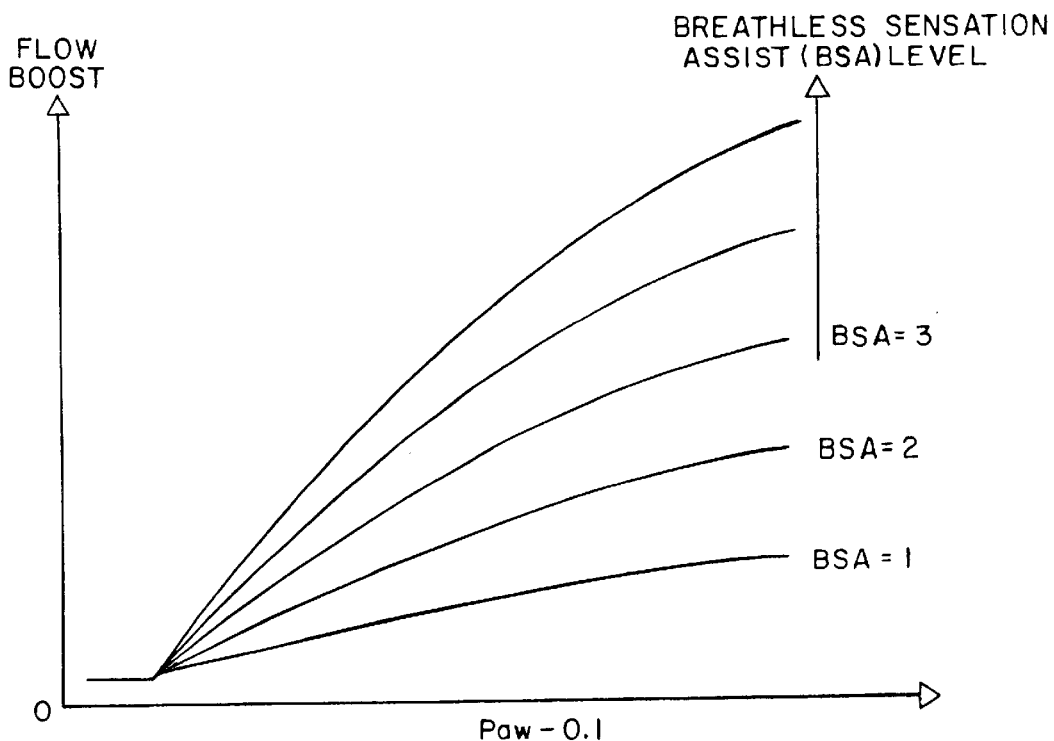
FIG. 3 illustrates the relationship between flow boost magnitude and the measured Paw-0.1 and user selected BSA level.

FIGS. 1 to 4 of the drawings illustrate a pressure targeted ventilation system or breathing apparatus and method according to an exemplary embodiment of the invention in which pressure at the start of each inspiration is boosted to a predetermined level in order to alleviate any breathless sensation which may otherwise be encountered by a patient.

FIG. 1 illustrates a pressure targeted ventilator or breathing apparatus 10 for connection to a patient 12 via inspiratory line 14 and expiratory line 16. The apparatus is connected to a supply of breathing gas via input 18. The breathing gas may be compressed air, oxygen, or any other suitable gas mixture.

The apparatus includes a gas delivery unit 20 connected to the inspiratory line 14, and an expiratory unit 22 connected to the expiratory line 16 which controls exhaust of gases from the patient's lungs out through the exhaust port 24. The gas delivery unit and expiratory unit are both connected to a control unit or microprocessor 26 which is programmed to control the start and end of inspiratory and expiratory phase of each breath, as well as the pressure of gas supplied to the patient during the inspiratory phase. Flow sensors 28,29 are provided in the inspiratory line 14 and expiratory line 16, and the outputs of these sensors are connected to the control unit 26. A pressure sensor or gauge 30 is provided in the apparatus or in the patient's airway for detecting patient airway pressure, as is known in the field. The output of pressure sensor 30 is also connected to the control unit 24. A manual BSA level input device 32 is provided on the housing of apparatus 10 to allow the user, such as a physician or other medical personnel, to adjust a boost pressure or breathless sensation assist (BSA) level to be provided during the inspiratory phase, as will be described in more detail below. The input device 32 is also connected to control unit 26.

The breathing apparatus starts to deliver gases to a patient 12 through gas delivery unit 20 at predetermined time or when the control unit detects a spontaneous patient effort through pressure gauge 30 or flow sensors 28,29. In conventional pressure targeted ventilation, the control unit is programmed to try to reach a pre-set target level and maintain that level throughout inspiration, as determined by the output of pressure gauge 30. This produces a quasi-square pressure waveform, as indicated by the solid line in FIG. 2a. The control unit will control the gas delivery unit and expiratory units so that delivered gases go into the patient's lungs. When the breath reaches the set inspiratory time (pressure control breath) or the flow or pressure detected meets the predetermined breath ending criteria (pressure support breath), the control unit 26 terminates the gas delivery and controls the expiratory unit 22 so that the gases in the patient's lungs can be exhaled out through the exhaust port 24.

Figure 4:
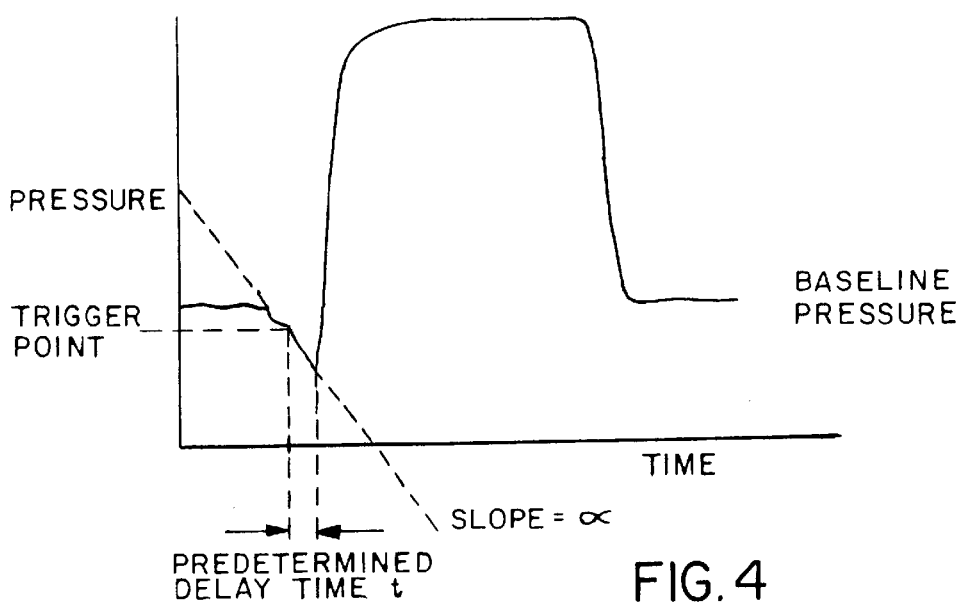
FIG. 4 illustrates the measurement of Paw-0.1.

The ventilator or breathing apparatus of this invention is arranged to boost the pressure of gas supplied to the patient at the start of each inspiratory cycle, based both on a user input at BSA level input device 32, and a measurement of the patient airway occlusion pressure, as illustrated in FIGS. 3 and 4. The arrangement is such that the pressure target level is boosted at the start of inspiration, as indicated by the dotted line in FIG. 2a, and then gradually tapers down to the pre-set target level. It will be understood that the boost level indicated in FIG. 2a is just one possible example, and larger or smaller pressure boost levels may be used in other cases, based on the input and patient criteria. In the illustrated example, the boosted pressure is gradually tapered down to the user-set target pressure level during the middle of the inspiratory phase, and there is no pressure boost during the latter phase of inspiration. The rate of taper of the boosted pressure back to the pre-set pressure may be faster or slower than in the illustrated example. The solid line in FIG. 2b illustrates the gas flow to the patient as a result of the pre-set or target pressure illustrated in solid line in FIG. 2b, while the dotted line illustrates the resultant flow boost of gas supplied to the patient as a result of the pressure boost of FIG. 2a. It will be understood that the control unit may alternatively be programmed to boost gas flow directly, rather than boosting pressure. This can be done by monitoring the flow rate at the flow sensor 28, and increasing the flow rate to a predetermined boost level at the start of inspiration, for example, the flow level indicated in dotted line in FIG. 2b.

The present invention uses the known relationship between breathless sensation and patient inspiratory muscle pressure, or Pmus. It is known that the breathless sensation encountered by patients is s a result of the gas flow being less than expected for a particular patient Pmus, and that it occurs mainly at the early phase of inspiration. Based on this principle, boosting the flow delivery (mainly at the beginning of inspiration) in proportion to Pmus during pressure controlled breaths or pressure supported breaths will alleviate patient's breathless sensation.

Research on the relationship between the airway occlusion pressure and Pmus have shown a good consistency between the two pressures at the beginning of the inspiration. When the patient starts an inspiratory effort against the occluded airway, the Paw at 0.1 second after the onset of the inspiratory effort (Paw-0.1) is comparable to the Pmus at 0.1 second after the onset of the inspiratory effort (Pmus-0.1) (Conti G, et al., American Journal of Respiration and Critical Care Medicine 1996; 154:907–912). This means that the boosting of ventilator flow delivery in proportion to the airway occlusion pressure, or Paw0.1, at the beginning of inspiration, can relieve the breathless sensation of ventilated patients. It is worth noting that Pmus-0.1 is also an indicator of the magnitude of the patient inspiratory effort.

In the exemplary embodiment of this invention, a user-adjustable Breathless Sensation Assist (BSA) level is included. The magnitude of flow boost at a given level of Pmus, or Paw-0.1, will be determined by the user-set BSA level. In principle, the higher the set BSA level, the higher the magnitude of flow boost. In the same way, the higher the Paw-0.1, the higher the magnitude of flow boost (FIG. 3). Thus, $$\text{Flow Boost} = f(BSA \text{ level}, Paw\text{-}0.1) \tag{1}$$

For the convenience of the control system design, the ventilator will boost its pressure target level (as illustrated in FIG. 2a), rather than boost its flow level, on the basis of pressure targeted ventilation. It is well known that the respiratory system can be approximated by a single-order motion equation (2). At the early phase of inspiration, because the volume-related recoil pressure (i.e., E×Volume) in Equation (2) is not a significant portion, Equation (2) can be approximated as:

$$Pmus + Paw = R \times Flow + E \times Volume \text{ where } Paw \text{ is the patient airway pressure, } R \text{ is airway resistance and } E \text{ is respiratory elastance} \tag{2}$$

$$Pressure = Flow \times R \tag{3}$$

Substituting Equation (1) into Equation (3) yields:

$$\text{Pressure boost} = f(BSA \text{ level}, Paw\text{-}0.1, R) \tag{4}$$

Equation (4) indicates that, the higher the BSA level or the Paw-0.1, or R, the higher the magnitude of pressure boost, and vice versa. In other words, the pressure boost magnitude is increased with the increase of Paw-0.1, BSA level, or airway resistance.

If the set BSA level is 0, the breath will be delivered in accordance with the conventional application of pressure targeted ventilation. In other words, the ventilator will target and maintain the user-set pressure level throughout the inspiration, as indicated by the solid line in FIG. 2a. When the BSA level is set higher than 0, the ventilator will target the user-set pressure target level plus the pressure boost magnitude at the beginning of inspiration (the dotted line in FIG. 2a). The magnitude of the pressure boost is calculated using Equation (4), i.e. the relationship illustrated in FIG. 3.

The pressure boost magnitude is gradually tapered down to the user-set target pressure level around the middle of inspiration (based on the inspiratory flow information or the set inspiratory time). The Paw is maintained at the user-set target level during the latter phase of inspiration. In order to minimize the control error and maximize the patient safety, there is an upper limit of pressure boost magnitude set by the control unit.

The ventilator intermittently measures Paw-0.1 value. Paw-0.1 can be measured, for example, by delaying the onset of inspiratory gas delivery for a predetermined time (usually 0.1 second) after the ventilator is triggered. This allows for a reliable Paw-0.1 measurement without causing significant patient awareness or discomfort. The resultant Paw signal is input to the control unit. A typical Paw variation with time is illustrated in FIG. 4, indicating the delay after triggering the ventilator. The ventilator analyzes the most linear segment of the Paw signals during this brief delay of gas delivery. Paw-0.1 is estimated by calculating the linear regression slope and extrapolating the regression line back to the pressure at the time of 0.1 second after start of patient inspiratory effort. The pressure signals are obtained from the pressure gauge 30. The intermittent measurement of Paw-0.1 may be conducted, for example, every 20 breaths or every 2 minutes. In order to minimize the error of the Paw-0.1 measurement, a running average of two or more measurements could be used, instead of using the Paw-0.1 value from a single breath.

Airway resistance may also be monitored by the control unit in order to vary the boost pressure magnitude. Airway resistance can be measured by many already-established methods, such as end-inspiratory pause method, isovolume method, and multi linear regression. For simplification purposes, the airway resistance can be simply calculated by dividing the pressure at the end of inspiration, as provided by pressure sensor 30, by the peak expiratory flow, as provided by flow sensor 29. Although this method does not provide for a very accurate airway resistance calculation, the fact that the BSA level is adjusted by users based on the degree of patient breathless sensation allows for more error in the calculation of airway resistance than other applications of airway resistance value.

As noted above, the BSA level is user-adjustable at manual control device 32. The range of BSA level may be represented, for example, by 0 to 10. The user chooses a BSA level that makes his patient feel the most comfortable. The ventilator will decide the magnitude of pressure boost based on the BSA setting, Paw-0.1, and airway resistance. When BSA level is set at 0, the ventilatory support will be delivered in accordance with the conventional application of pressure targeted ventilation. If the BSA level is set higher than 0, pressure boost will be in effect on the basis of pressure target breath. The higher the set BSA level, the higher the pressure boost for any given level of Paw-0.1 and airway resistance. If the Paw-0.1 increases while BSA and airway resistance remain constant, the ventilator will increase its pressure boost. A decrease in Paw-0.1 under the same conditions results in the opposite response.

If the user sets the BSA level at 0, the ventilator's control unit 26 will deliver pressure targeted breath as usual, i.e., trying to achieve a quasi-square waveform of Paw based on the output signal from the pressure gauge 30. If the BSA level is set higher than 0, the control unit 26 will measure Paw-0.1 (as illustrated in FIG. 4) and the airway resistance at the first breath. From the second breath, the control unit 26 will boost its pressure target by using the measured Paw-0.1, the measured airway resistance and the user-set BSA level. Thus, the real target pressure will be the user-set target pressure plus the pressure boost magnitude determined by the control unit 26.

The control unit 26 will compute a running average of the breath-by-breath calculation of airway resistance using Paw at the end of inspiration and peak expiratory flow Intermittently, the control unit will measure Paw-0.1 as described above and determine the magnitude of pressure boost based on the newest information of Paw-0.1 and airway resistance, together with the BSA level setting.

After Paw (from pressure gauge 30) reaches the desired level that is determined by the control unit 26 (i.e., pre-set pressure plus the boost pressure), the control unit will control the gas delivery unit 20 in such a way as to gradually taper Paw down to the user-set target pressure level around the middle of inspiration. There is no pressure boost during the latter phase of inspiration. When the duration of inspiration reaches the set inspiratory time (pressure control breath) or the flow or pressure measurement meets the predetermined breath ending criteria (pressure support breath), the control unit 26 terminates the gas delivery and controls expiratory unit 22 so that the gases in the patient's lungs can be exhaled out through the exhaust port 24.

Several variations of the above described apparatus could easily be realized by those skilled in the art. For instance, the flow sensors 28 and 29 could be replaced by a flow sensor placed at the patient airway. Also, the pressure sensing site could be inside the apparatus 10 or inside the patient 12. The Paw tapering-down speed and the timing when the Paw reaches the user-set target pressure level could be varied from those illustrated and described above. Also, other methods may be used to calculate Pmus or Paw-0.1, though these methods are often more complicated and time-consuming. Paw-0.1 can be measured by reducing trigger sensitivity. It is also possible to directly boost flow instead of boosting pressure. This invention can also be implemented in dual control modes where the target pressure level of a breath is automatically adjusted over a number of breaths (not within a breath) within the predetermined range so that the gas volume delivered to the patient meets the set target volume (e.g., volume support ventilation, or volume targeted pressure support ventilation).

The breathing apparatus and method of this invention can alleviate some or all of the discomfort sometimes experienced by patients as a result of a breathless sensation. The pressure of gas supplied to the patient is boosted by a predetermined amount at the start of the inspiratory phase of each breath, using a control unit which determines the boost pressure magnitude based on a user input level, a patient airway occlusion pressure, and airway resistance. The control unit constantly monitors these values in order to vary the boost pressure magnitude as necessary in subsequent breaths. By providing a user input device for varying the boost pressure magnitude, a BSA level can be chosen which makes the patient feel most comfortable. This system and method takes into account the patient's own inspiratory effort when controlling the amount of pressure boost, while still providing ventilator control of the overall inspiratory cycle to avoid the risk of underventilation or overventilation, as can sometimes occur with proportional assist ventilation. This invention can provide a more secure level of ventilatory support than proportional assist ventilation, while still allowing the patient's inspiratory effort to play a role in ventilatory control through an increased or boosted pressure at the early phase of each inspiration.

Although an exemplary embodiment of the invention has been described above by way of example only, it will be understood by those skilled in the field that modifications may be made to the disclosed embodiment without departing from the scope of the invention, which is defined by the appended claims.

I claim:

1. A breathing apparatus to provide positive airway pressure assist, comprising:

a gas delivery unit having an input for connection to a source of breathing gas and an output;

an inspiration line connected to the output of the gas delivery unit for connecting the gas delivery unit to a patient during an inspiratory phase of each breath;

an expiratory unit for controlling exhaling of gases from the patient during an expiratory phase of each breath;

an expiratory line having an output connected to the expiratory unit and an input for connection to a patient;

sensor means for sensing a parameter associated with patient breathlessness;

a control unit connected to the gas delivery unit, expiratory unit, and sensor means for controlling pressure of gas supplied to a patient during each inspiratory phase and controlling exhalation of gas from the patient during each expiratory phase, the pressure of gas supplied during each inspiratory phase being based on a pre-set target pressure;

the control unit including program means for periodically determining a level of patient breathlessness based on the output of the sensor means, means for using the determined patient breathlessness level to calculate a boost-pressure level higher than the pre-set target pressure, means for operating the control unit to boost the pressure of gas supplied to the patient at the start of each inspiratory phase to the calculated boost pressure level in order to reduce patient breathlessness, and means for reducing the boost pressure of gas supplied to the patient back to the pre-set target pressure at a predetermined time after the start of each inspiratory phase and prior to the end of the inspiratory phase.

2. The apparatus as claimed in claim 1, wherein the means for determining the level of patient breathlessness comprises means for measuring patient airway occlusion pressure at periodic intervals, and for increasing the boost pressure level in response to increase in patient airway occlusion pressure.

3. The apparatus as claimed in claim 1, wherein the program includes means for operating the control unit to taper the pressure supplied to the patient from the boost pressure level back to the pre-set target pressure at approximately the Middle of the inspiratory phase of each breath.

4. A positive airway pressure breathing system, comprising:
   a gas delivery unit having an input for connection to a source of breathing gas and an output;
   an inspiration line connected to the output of the gas delivery unit for connecting the gas delivery unit to a patient during an inspiratory phase of each breath;
   an expiratory unit for controlling exhaling of gases from the patient during an expiratory phase of each breath;
   an expiratory line having an output connected to the expiratory unit and an input for connection to a patient;
   a pressure sensor for sensing pressure in the system;
   a control unit connected to the gas delivery unit, expiratory unit, and pressure sensor for controlling pressure of gas supplied to a patient in each inspiratory phase and exhaling of gas from the patient during each expiratory phase, the pressure of gas during each inspiratory phase being based on a pre-set target pressure;
   a user input device connected to the control unit for user input of a selected breathless sensation assist level; and
   a program associated with the control unit for operating the control unit, the program comprising means for periodically determining the degree of patient breathlessness from the pressure sensor output, means for calculating a boost pressure level higher than the pre-set target pressure, the boost pressure level being a function of the determined degree of patient breathlessness and the user selected breathless sensation assist level, and means for operating the control unit to boost the pressure of gas supplied to the patient at the start of each inspiratory phase to the calculated boost pressure level to reduce patient breathlessness, and to reduce the pressure of gas supplied to the patient back to the pre-set target pressure at a predetermined time after the start of the inspiratory phase and prior to the end of the inspiratory phase.

5. The apparatus as claimed in claim 4, wherein the program further comprises means for detecting a user input breathless sensation assist level of zero, and for operating the control unit to supply gas at the pre-set target pressure for the entire inspiratory phase on detection of a zero input at the user input device.

6. A breathing apparatus for providing positive airway pressure assistance, comprising:
   a gas delivery unit having an input for connection to a source of breathing gas and an output;
   an inspiration line connected to the output of the gas delivery unit for connecting the gas delivery unit to a patient during an inspiratory phase of each breath;
   an expiratory unit for controlling exhaling of gases from the patient during an expiratory phase of each breath;
   an expiratory line having an output connected to the expiratory unit and an input for connection to a patient;
   a pressure sensor for sensing pressure in the system;
   a control unit connected to the gas delivery unit, expiratory unit, and pressure sensor for controlling supply of gas to a patient in each inspiratory phase and exhaling of gas from the patient during each expiratory phase, the supply of gas during each inspiratory phase being based on a pre-set target pressure;
   a user input device connected to the control unit for user input of a selected breathless sensation assist level; and
   a program associated with the control unit for operating the control unit, the program comprising means for determining the level of patient breathlessness at predetermined intervals by measuring patient airway occlusion pressure, means for calculating a boost pressure level higher than the pre-set target pressure based on the user input breathless sensation assist level and the determined level of patient breathlessness, means for operating the control unit to boost the pressure of gas supplied to the patient at the start of each inspiratory phase to the calculated boost pressure level in order to reduced patient breathlessness, and to reduce the pressure of gas supplied to the patient back to the pre-set target pressure at a predetermined time after the start of the inspiratory phase and prior to the end of the inspiratory phase.

7. The apparatus as claimed in claim 6, wherein the program includes means for calculating airway resistance, and means for varying the boost pressure level as a function of the user selected breathless sensation assist level, the measured patient airway occlusion pressure, and the calculated airway resistance.

8. A method of controlling the inspiratory phase in a positive pressure assist breathing system in order to relieve patient breathlessness, comprising the steps of:
   setting a target pressure for pressure of gas supplied to the patient during the inspiratory phase;
   determining a boost pressure of gas to be supplied to the patient which is higher than the pre-set target pressure;
   periodically determining the level of patient breathlessness and adjusting the boost pressure in response to changes in the level of patient breathlessness;
   boosting the pressure of gas supplied to the patient to the most recently determined boost pressure at the start of each inspiratory phase in order to relieve any breathless sensation encountered by the patient; and
   gradually reducing the pressure of gas supplied to the patient from the boost pressure back to the pre-set target pressure at a predetermined point in the inspiratory phase prior to the end of the inspiratory phase.

9. The method as claimed in claim 8, wherein the step of determining an initial boost pressure comprises monitoring a breathless sensation assist (BSA) level entered by a user at a control device and varying the boost pressure based on the entered BSA level.

10. The method as claimed in claim 9, wherein no boost is added to the pre-set level of gas supplied to the patient if the user selected BSA level is zero.

11. The method as claimed in claim 8, wherein the step of periodically determining the level of patient breathlessness comprises measuring the patient airway occlusion pressure at a predetermined point in inspiration and adjusting the boost pressure to be used for the next inspiratory phase in response to any change in patient breathlessness level.

12. The method as claimed in claim 9, including the step of calculating the patient airway resistance and increasing the boost level in response to increase in patient airway resistance.

13. The method as claimed in claim 9, wherein the step of determining a boost level comprises determining a boost pressure level higher than the set target pressure level, the step of boosting the level of gas comprises monitoring the pressure in the system with a pressure sensor, and boosting the pressure until the predetermined boost pressure level is reached, and the step of reducing the level of gas supplied to the patient comprises reducing the pressure from the boost pressure level back to the set target pressure level.

14. A method of controlling the inspiratory phase in a pressure targeted ventilation system, comprising the steps of:
   setting a target pressure level for the inspiratory phase;
   determining a boost level of gas to be supplied to the patient which is higher than the pre-set target pressure level;
   boosting the pressure of gas supplied to the patient to the determined level higher than the pre-set target level at the start of the inspiratory phase in order to relieve any breathless sensation encountered by the patient;
   gradually reducing the pressure of gas supplied to the patient from the boost pressure back to the pre-set target pressure at a predetermined point in the inspiratory phase prior to the end of the inspiratory phase;
   the step of determining a boost level comprising monitoring a breathless sensation assist (BSA) level entered by a user at a control device and varying the boost level based on the entered BSA level, and further comprising periodically determining the patient airway occlusion pressure at a predetermined point in inspiration and increasing the boost level in response to an increase in patient airway occlusion pressure; and
   the patient airway occlusion pressure being measured at predetermined intervals, each patient airway occlusion pressure measurement being taken at approximately 0.1 seconds after the start of a patient inspiratory effort.

15. The method as claimed in claim 14, wherein the patient airway occlusion pressure is measured at intervals corresponding to a predetermined number of breaths.

16. A method of controlling the inspiratory phase in a pressure targeted ventilation system, comprising the steps of:
   setting a target pressure level for the inspiratory phase;
   determining a boost level of gas to be supplied to the patient which is higher than the pre-set target pressure level;
   boosting the pressure of gas supplied to the patient to the determined boost level higher than the pre-set target level at the start of the inspiratory phase in order to relieve any breathless sensation encountered by the patient;
   gradually reducing the pressure of gas-supplied to the patient from the boost pressure back to the pre-set target pressure at a predetermined point in the inspiratory phase prior to the end of the inspiratory phase;
   the step of determining a boost level comprising monitoring a breathless sensation assist (BSA) level entered by a user at a control device and varying the boost level based on the entered BSA level, and further comprising periodically determining the patient airway occlusion pressure at a predetermined point in inspiration and increasing the boost level in response to an increase in patient airway occlusion pressure; and
   the patient airway occlusion pressure being measured at predetermined intervals, each patient airway occlusion pressure measurement being taken at a predetermined time interval after the start of a patient inspiratory effort.

17. A method of controlling the inspiratory phase in a pressure targeted ventilation system, comprising the steps of:
   setting a target pressure level for the inspiratory phase;
   determining a boost level of gas to be supplied to the patient which is higher than the pre-set target pressure level;
   boosting the pressure of gas supplied to the patient to the determined boost level higher than the pre-set target level at the start of each inspiratory phase in order to relieve any breathless sensation encountered by the patient;
   gradually reducing the pressure of gas supplied to the patient from the boost pressure level back to the pre-set target pressure level at a predetermined point in the inspiratory phase prior to the end of the inspiratory phase;
   the step of determining a boost pressure level comprising monitoring a breathless sensation assist (BSA) level entered by a user at a control device and varying the boost pressure level based on the entered BSA level, and further comprising periodically determining the degree of patient breathlessness at a predetermined point in inspiration and adjusting the boost pressure level in response to a change in the determined degree of patient breathlessness; and
   the degree of patient breathlessness being measured at a predetermined intervals after the start of a patient inspiratory effort.

18. A pressure targeted ventilation system, comprising:
   a gas delivery unit having an input for connection to a source of breathing gas and an output;
   an inspiration line connected to the output of the gas delivery unit for connecting the gas delivery unit to a patient during an inspiratory phase of each breath;
   a pressure controller for controlling the pressure of gas supplied to a patient during each inspiratory phase;
   an expiratory unit for controlling exhaling of gases from a patient during an expiratory phase of each breath;
   a user input device connected to the pressure controller for user input of a selected breathless sensation assist (BSA) level;
   sensor means connected to the pressure controller for sensing the level of patient breathlessness during an inspiratory phase;
   the pressure controller including means for setting a target pressure level for the inspiratory phase, means for determining a boost level of gas to be supplied to the patient which is higher than the pre-set target pressure level, means for boosting the pressure of gas supplied to the patient to the determined boost pressure level higher than the pre-set target level at the start of each inspiratory phase in order to relieve any breathless sensation encountered by the patient, and means for gradually reducing the pressure of gas supplied to the patient from the boost pressure back to the pre-set target pressure at a predetermined point in the inspiratory phase prior to the end of the inspiratory phase;
   the means for determining a boost level comprising means for monitoring the breathless sensation assist (BSA) level entered by a user at the user input device and varying the boost level based on the entered BSA level, and further comprising means for periodically determining the patient breathlessness level at a predetermined point in inspiration and increasing the boost pressure level in response to an increase in the determined patient breathlessness level; and the means for determining patient breathlessness level comprising means for measuring a parameter which is a function of patient breathlessness at predetermined intervals, each measurement being taken at a predetermined time interval after the start of a patient inspiratory effort.

19. A pressure targeted ventilation system, comprising:

a gas delivery unit having an input for connection to a source of breathing gas and an output;

an inspiration line connected to the output of the gas delivery unit for connecting the gas delivery unit to a patient during an inspiratory phase of each breath;

a pressure controller for controlling the pressure of gas supplied to a patient during each inspiratory phase;

an expiratory unit for controlling exhaling of gases from a patient during an expiratory phase of each breath;

a user input device connected to the pressure controller for user input of a selected breathless sensation assist (BSA) level;

a pressure sensor for sensing pressure in the system;

the pressure controller including means for setting a target pressure level for the inspiratory phase, means for determining a boost level of gas to be supplied to the patient which is higher than the pre-set target pressure level, means for boosting the pressure of gas supplied to the patient to the determined boost pressure level higher than the pre-set target level at the start of each inspiratory phase in order to relieve any breathless sensation encountered by the patient, and means for gradually reducing the pressure of gas supplied to the patient from the boost pressure back to the pre-set target pressure at a predetermined point in the inspiratory phase prior to the end of the inspiratory phase;

the means for determining a boost level comprising means for monitoring the breathless sensation assist (BSA) level entered by a user at the user input device and varying the boost level based on the entered BSA level, and further comprising means for periodically determining the patient airway resistance and adjusting the boost pressure level in response to a change in the patient airway resistance.

* * * * *